United States Patent [19]

Schaefer et al.

[11] Patent Number: 4,844,826

[45] Date of Patent: Jul. 4, 1989

[54] USE OF ORGANOSILICON COMPOUNDS TO THICKEN OILS

[75] Inventors: Dietmar Schaefer; Klaus Hoffmann, both of Essen, Fed. Rep. of Germany

[73] Assignee: Th. Goldschmidt AG, Fed. Rep. of Germany

[21] Appl. No.: 245,824

[22] Filed: Sep. 16, 1988

[30] Foreign Application Priority Data

Oct. 9, 1987 [DE] Fed. Rep. of Germany ....... 3734217

[51] Int. Cl.$^4$ ................ C10M 115/04; C10M 139/02
[52] U.S. Cl. ............................... 252/49.6; 106/287.14
[58] Field of Search ................... 252/49.6; 106/287.14

[56] References Cited

U.S. PATENT DOCUMENTS

| | | | |
|---|---|---|---|
| 4,115,343 | 9/1978 | Guillaume et al. | 252/49.6 |
| 4,248,724 | 2/1981 | MacIntosh | 252/49.6 |
| 4,564,467 | 1/1986 | Rauline | 252/49.6 |
| 4,652,386 | 3/1987 | Alberts et al. | 252/49.6 |
| 4,780,245 | 10/1988 | Burke et al. | 106/287.14 |

Primary Examiner—Jacqueline V. Howard
Attorney, Agent, or Firm—Toren, McGeady & Associates

[57] ABSTRACT

Thickeners of the general formula

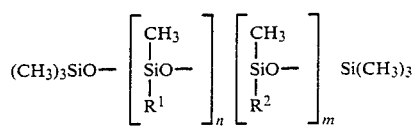

wherein
$R^1$ is alkyl with 18 to 36 carbon atoms,
$R^2$ is hydrogen, methyl or a group of the general formula $-(CH_2)_xR^3$,
$R^3$ being a $COOR^4$ group, in which $R^4$ is hydrogen or alkyl with 1 to 4 carbon atoms, or
a $-O[C_rH_{2r}O-]_yR^5$ group, in which $R^5$ is hydrogen, alkyl with 1 to 4 carbon atoms or acyl, $r=2$ or 3 and $y \geq 0$,
$x=2$ to 12,
$n \geq 20$ and $m=0$ to $0.5n$, are disclosed for hydrocarbon oils, ester oils and vegetable oils. The thickeners are incorporated in the oil in amounts of 2 to 10% by weight, based on the oil.

The organopolysiloxanes, effective as thickeners, are usable for many purposes, are effective in small concentrations and are physiologically safe. They are therefore suitable for thickening cosmetic or pharmaceutical preparations based on hydrocarbons, ester oils and vegetable oils.

9 Claims, 8 Drawing Sheets

USE OF ORGANOSILICON COMPOUNDS TO THICKEN OILS

FIELD OF INVENTION

The invention generally relates to thickeners for oils and is particularly directed to a method of thickening hydrocarbon oils, ester oils and vegetable oils (hereafter sometimes collectively "oils") with selected organopolysiloxanes with long-chain alkyl groups linked to the silicon atoms, and to the oils obtained as a result of the method.

BACKGROUND INFORMATION AND PRIOR ART

Thickeners for nonaqueous systems, particularly thickeners for mineral oils, ester oils and vegetable oils are used especially in cosmetics and for the production of lubricants. Different thickeners are used, depending on the use to which the thickened products are to be put.

As thickening agents for cosmetics are generally used higher fatty alcohols, fatty acids and their ethoxylation products, monoesters of fatty acids and glycerin, vegetable and other waxes, polymeric compounds and metal soaps. These thickeners must be skin-compatible and should not cause any interfering effects in respect to the intended use of cosmetic preparations into which the thickeners are incorporated.

To thicken lubricants, especially alkali, alkaline earth, zinc and aluminum stearates are used. Aromatic polyureas have also proven to be useful. Moreover, highly disperse silica, carbon black and prepared clay minerals, such as bentonites, ae used for the thickening of lubricants.

Thickeners are also used for the modification and/or stabilization of the viscosity of fuels and the preparation of incendiary compositions and burning charges for military purposes.

OBJECT OF THE INVENTION

It is an object of the present invention to provide new thickeners, which can be used for a multitude of purposes, are effective in the lowest possible concentrations and are physiologically safe and harmless, so that they can also be used in the cosmetic and pharmaceutical areas.

Another object of the invention is to provide a simple and effective method of thickening oils. Generally, it is an object of the invention to improve on the art of thickening non aqueous systems.

SUMMARY OF THE INVENTION

Surprisingly, it has been ascertained that selected modified organopolysiloxanes have thickening properties and exhibit effects which make them particularly suitable for use in cosmetics and pharmacy, but also in certain areas of technology.

These selected organopolysiloxanes have the general formula

I wherein
  $R^1$ is alkyl with 18 to 36 carbon atoms,
  $R^2$ is hydrogen, methyl or a group of the general formula $-(CH_2)_x R^3$,
    $R^3$ being a $COOR^4$ group, in which $R^4$ is hydrogen or alkyl with 1 to 4 carbon atoms, or
    a $-O[C_rH_{2r}O-]_y R^5$ group, in which $R^5$ is hydrogen, alkyl with 1 to 4 carbon atoms or acyl, r=2 or 3 and y≧0,
  x=2 to 12,
  n≧20 and m=0 to 0.5n.

These compounds are excellent thickeners for hydrocarbon oils, ester oils and vegetable oils if used in amounts of 2 to 10% by weight, based on the oils.

$R^1$ is alkyl with 18 to 36 cabon atoms, alkyls with 22 to 36 carbon atoms being preferred.

$R^2$ is hydrogen, methyl or a group of the general formula $-(CH_2)_x R^3$, in which x is a whole number from 2 to 12. $R^3$ either has the meaning of a $-COOR^4$ group or the meaning of a $-O[C_rH_{2r}O-]_y R^5$ group, in which $R^4$ is hydrogen or alkyl with 1 to 4 carbon atoms, $R^5$ is hydrogen, alkyl with 1 to 4 carbon atoms or acyl, especially acetyl and r has a value of 2 or 3. Both values for r can be present side by side in the average molecule and therefore fractional values between 2 and 3 are also possible. Finally, y is greater than or equal to 0.

The number of difunctional siloxy units n is greater than or equal to 20; m has a value of 0 to 0.5n.

The following structure formulas of typical and preferred compounds serve to explain further the structure of the modified organopolysiloxanes, which are to be used pursuant to the invention.

-continued

The compounds, which are to be used pursuant to the invention, can be synthesized by known methods from hydrogenmethylpolysiloxanes of the general formula

II wherein $v+w=n+m$, by the hydrosilylating addition reaction of alkenes with 18 to 36 carbon atoms and a terminal olefinic double bond and, optionally, compounds of the general formula $$CH_2=CH-(CH_2)_{x-2}R^3$$

in the presence of catalysts, especially platinum catalysts.

The modified organopolysiloxanes of the general formula I are waxy compounds. They dissolve in oils at temperatures above 40° C. On cooling to room temperature, the modified polysiloxanes, which are to be used pursuant to the invention, presumably form a skeletal crystalline structure in the oils, which may be the cause of the structural viscosity of the oils thickened pursuant to the invention. If shear forces are allowed to act on the thickened oils, for example, by means of a high-shear stirrer, the thickened preparations liquefy. With the renewed formation of the skeletal structure in the oil, its viscosity increases once again. The same effect may be observed when the preparation, thickened pursuant to the invention, is heated to a temperature above 40° C. Above this temperature range, the modified organopolysiloxane dissolves in the oil and the preparation essentially has the viscosity of the base oil. If the preparation is cooled to a temperature below the aforementioned temperature range, the structure, which causes the thickening, develops once again in the oil.

This behavior can be utilized especially in cosmetic or pharmaceutical preparations. For example, preparations may be produced, which have a high viscosity at room temperature, but liquefy when applied on the skin. As a result, they can easily be applied on the skin, distributed on the skin and, if necessary, rubbed into it.

The oils, thickened pursuant to the invention with the modified organopolysiloxanes, can easily be stirred with a spatula. They are soft and pliable. They are neither stringy nor tacky.

Paraffin oils and white spirit may be mentioned as examples of hydrocarbons, which are to be thickened pursuant to the invention.

Isooctyl stearate and isooctadecyl isononate are examples of ester oils.

Examples of vegetable oils are sunflower oil and soybean oil.

The thickeners, which are to be employed pursuant to the invention, are used in amounts of 2 to 10% by weight and preferably of 5 to 10% by weight, based on the oil.

In the following examples, the properties of the modified polysiloxanes, which are to be used pursuant to the invention, and the structural viscosity of the thickened oils are explained in greater detail. It is understood that the examples are given by way of illustration and not by way of limitation.

The viscosities were measured with a rotation viscosimeter (Rheomat 115 of Contraves AG, Zurich) according to DIN 125 (Module 7/7). In the examples, the viscosity is given as a function of the shear rate. At each velocity step, the viscosity is determined after 15 seconds. Between velocity steps, the thickened oils are not stressed mechanically for 15 seconds.

DESCRIPTION OF THE DRAWINGS

FIGS. 1–8 are viscosity graphs. In the graphic representation of FIGS. 1–8 of the viscosity (mPas) as a function of the shear rate (s$^{-1}$), it should be noted that the various velocity steps are passed through in the direction of the arrow.

EXAMPLE 1

A compound (5 g) of the general formula is dissolved at 80° C. in 95 g of paraffin oil that has an initital viscosity of about 150 mPas and cooled slowly without stirring.

Figure 1:
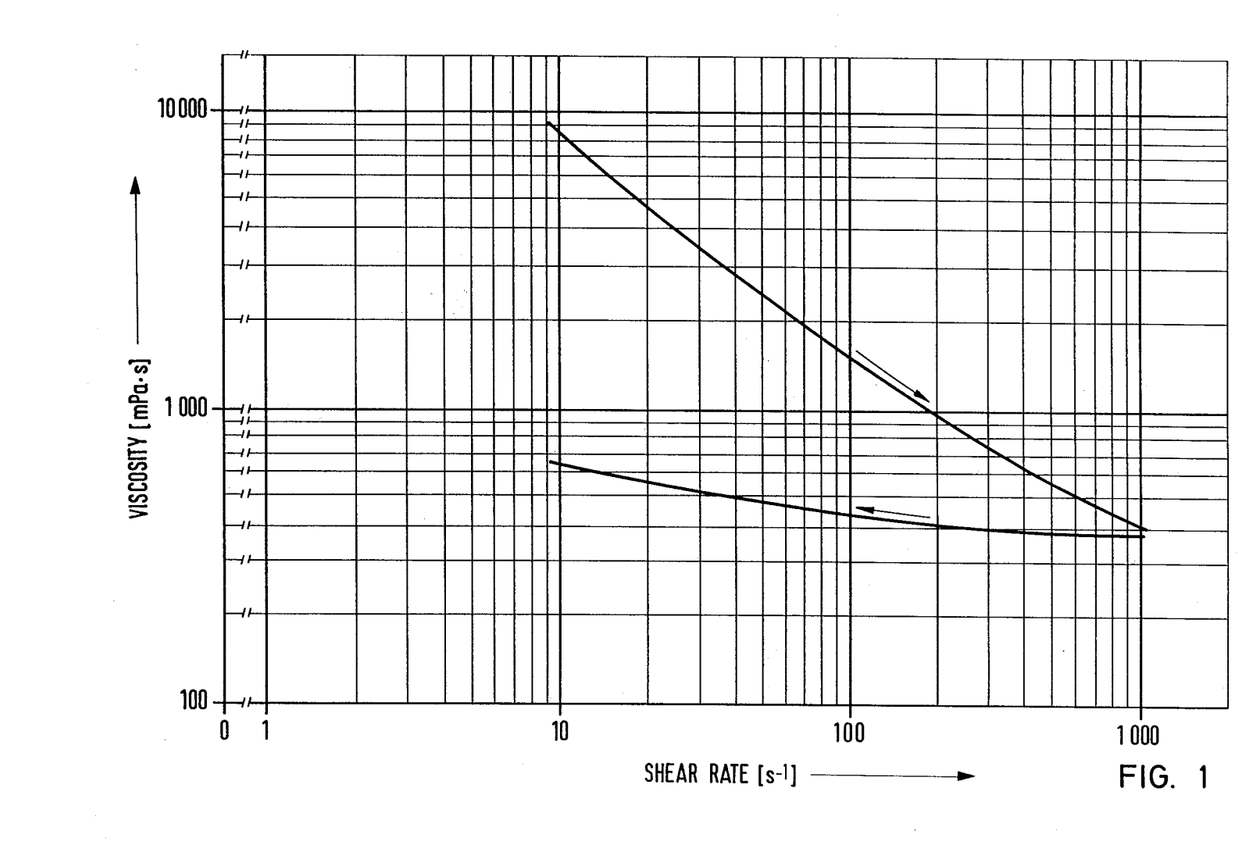

The viscosity of the thickened paraffin oil at 25° C. is shown as a function of the shear rate in FIG. 1.

EXAMPLE 2

Figure 2:
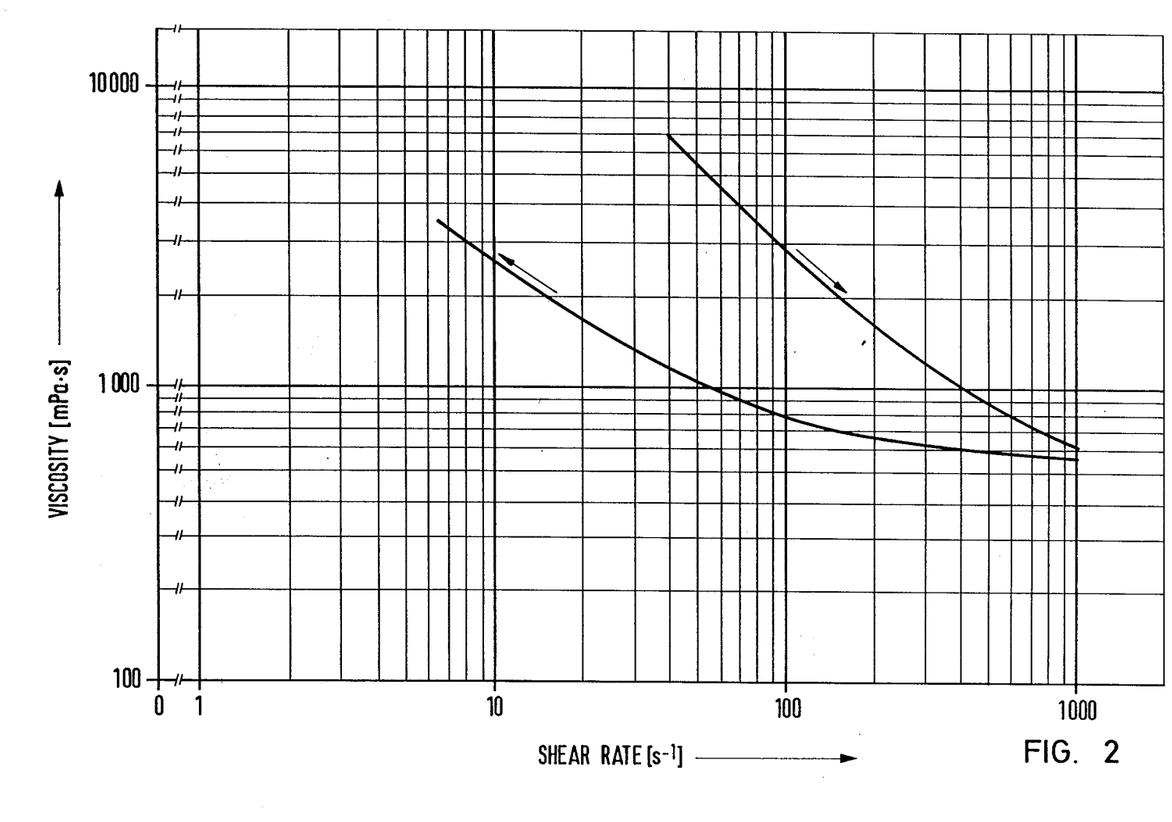

Example 1 is repeated. However, instead of the 5% solution, an 8% solution is investigated (FIG. 2).

EXAMPLE 3

Figure 3:
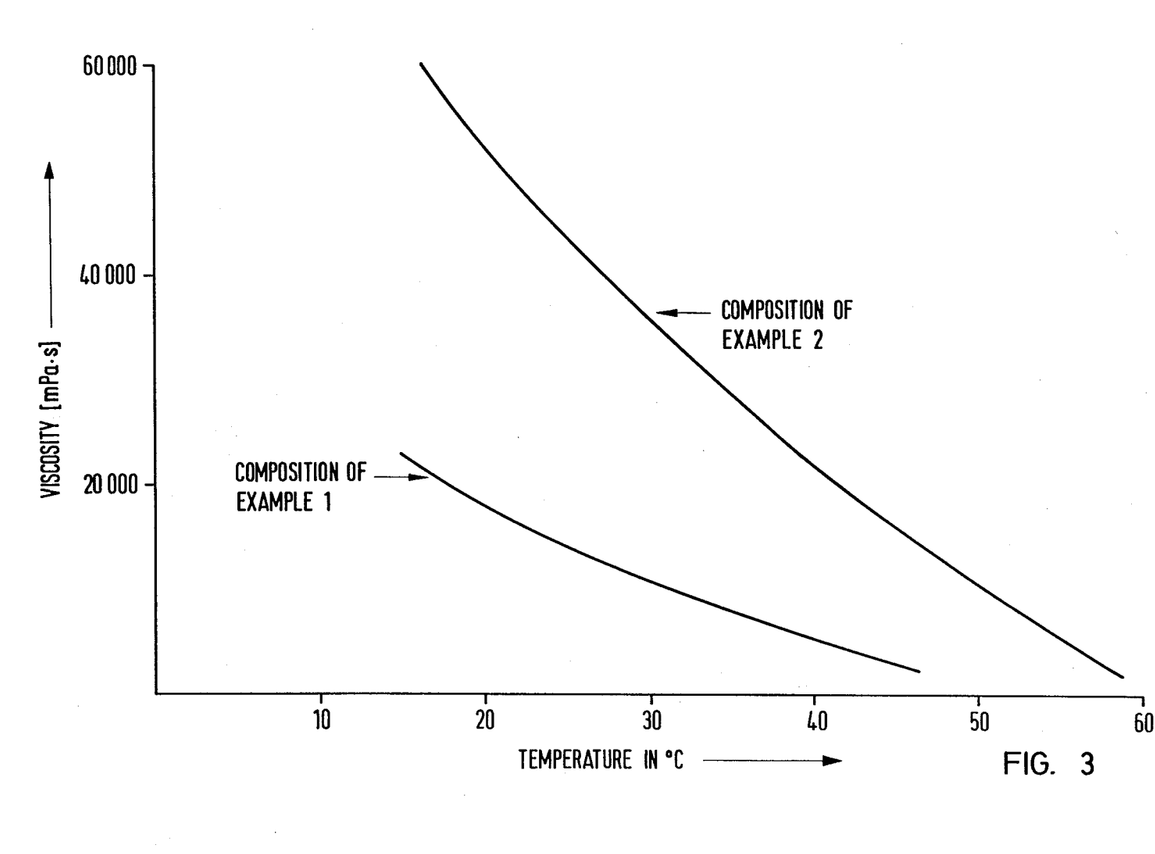

In this example, the effect of temperature on the viscosity of the paraffin oil, thickened pursuant to the invention, is investigated at a constant shear rate of 6.65 s$^{-1}$ (FIG. 3).

EXAMPLE 4

A compound (5 g) of the general formula is dissolved at 80° C. in 95 g of isooctyl stearate and cooled slowly without stirring.

Figure 4:
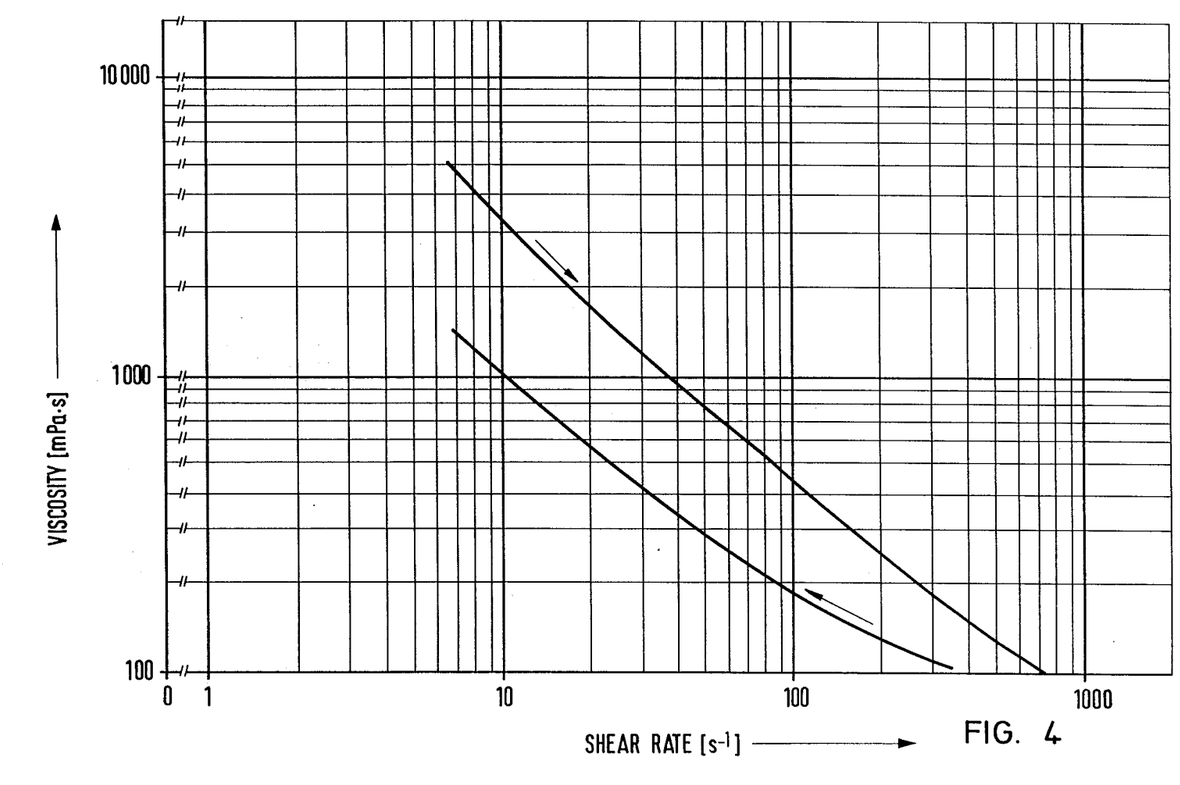

The viscosity of the thickened isooctyl stearate is shown as a function of the shear rate at 25° C. in FIG. 4.

EXAMPLE 5

A compound (5 g) of the general formula is dissolved at 80° C. in 95 g of isooctyl stearate and cooled slowly without stirring.

Figure 5:
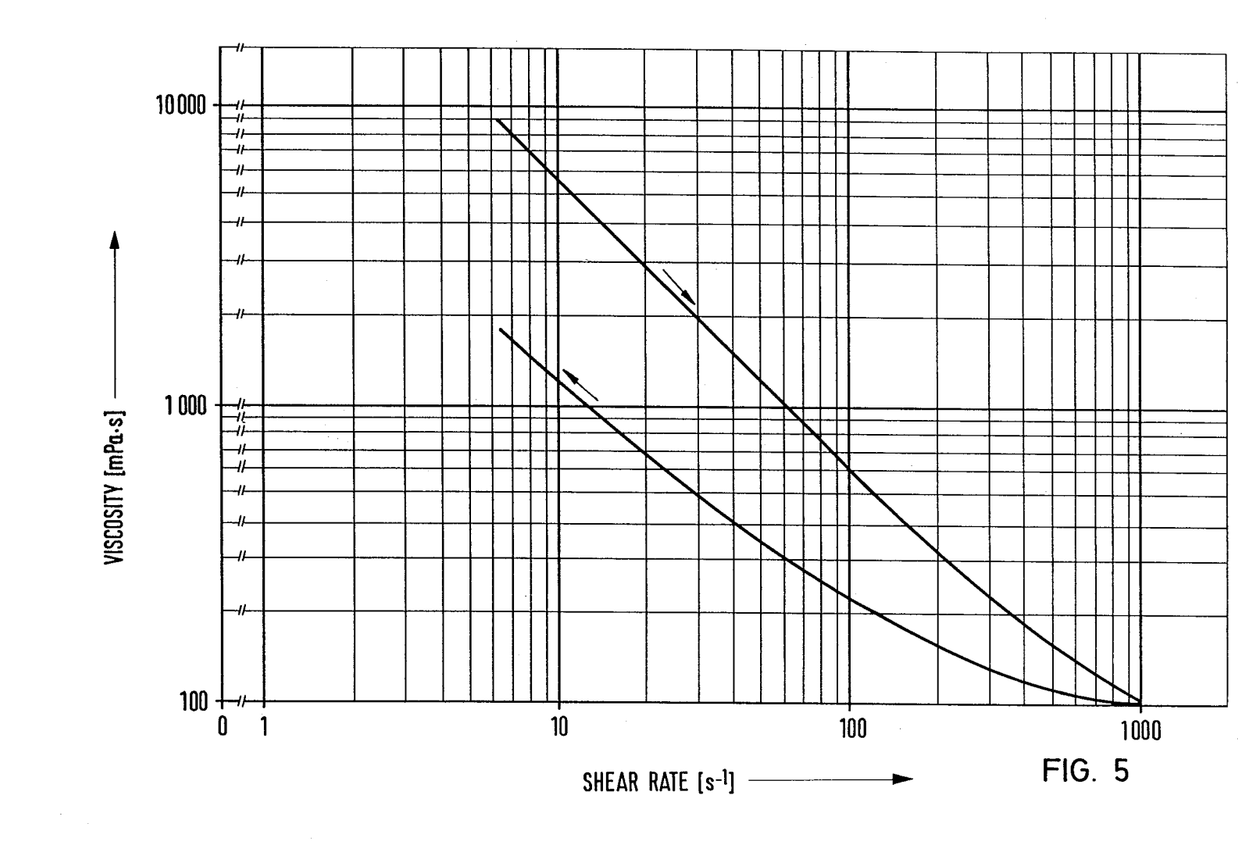

The viscosity of the thickened isooctyl stearate is shown as a function of the shear rate at 25° C. in FIG. 5.

EXAMPLE 6

A compound (5 g) of the general formula is dissolved at 80° C. in 95 g of paraffin oil that has a viscosity of about 150 mPas and cooled slowly without stirring.

Figure 6:
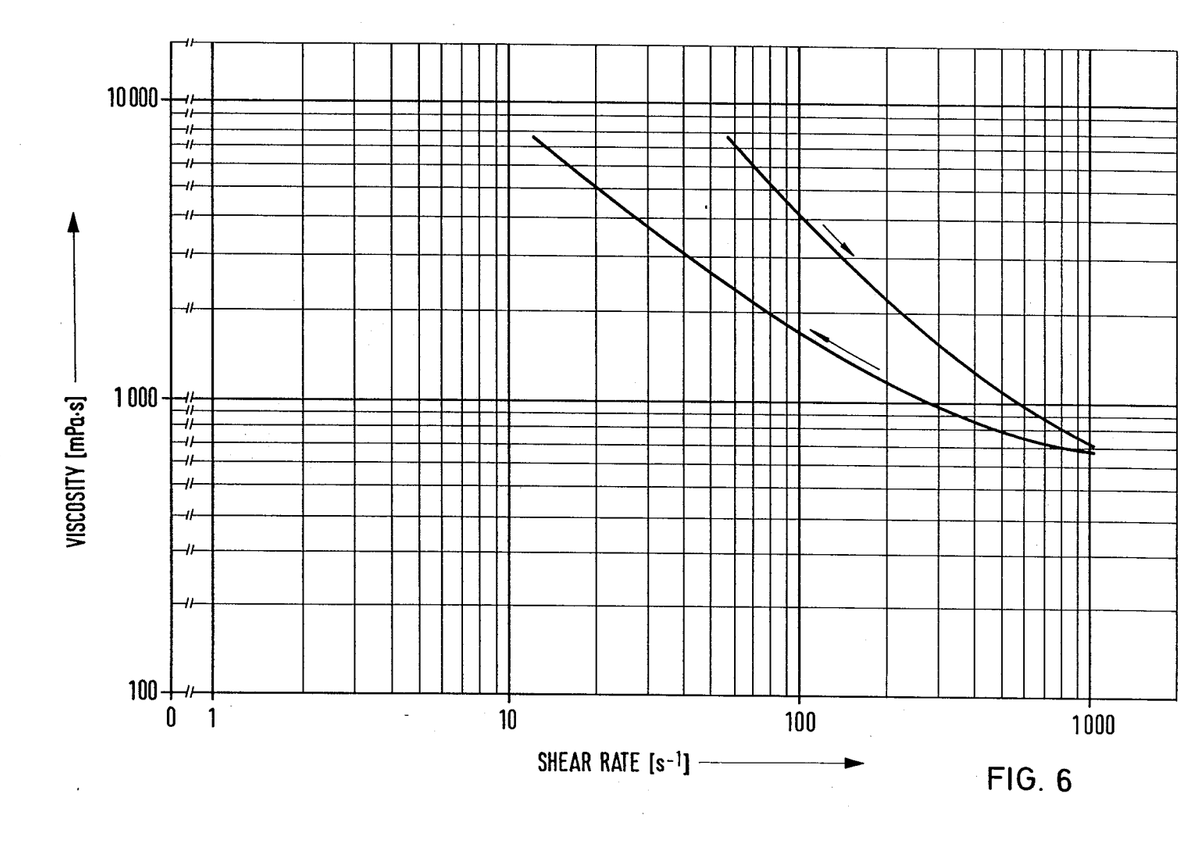

The viscosity of the thickened paraffin oil at 25° C. is shown as a function of the shear rate in FIG. 6.

EXAMPLE 7

Example 1 is repeated. However, the paraffin oil is replaced by solvent naphtha with a boiling point range of 145° to 200° C.

Figure 7:
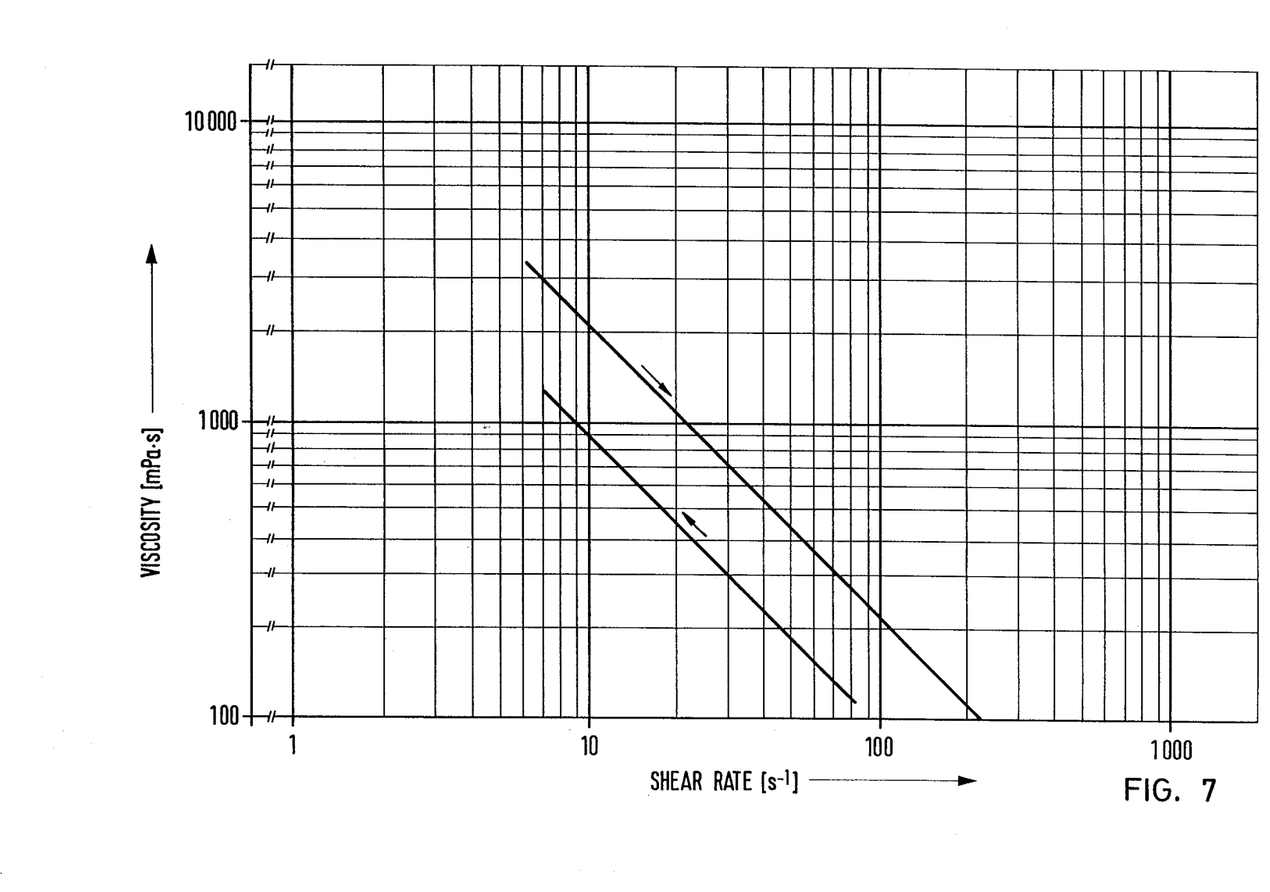

The viscosity of the thickened solvent naphtha at 25° C. is shown as a function of the shear rate in FIG. 7.

EXAMPLE 8

Example 6 is repeated. However, the paraffin oil is replaced by solvent naphtha with a boiling point range of 145° to 200° C.

Figure 8:
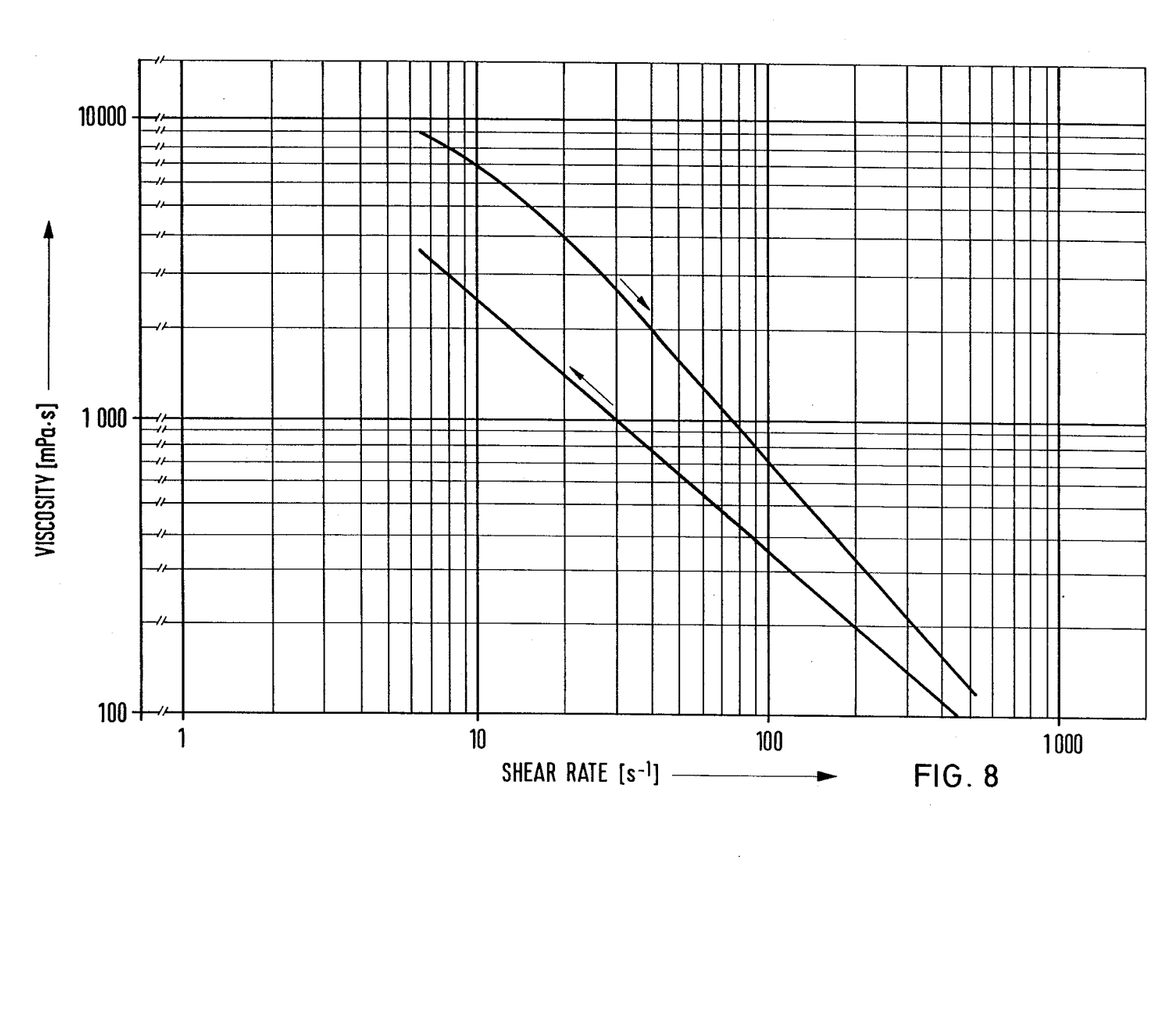

The viscosity of the thickened solvent naphtha at 25° C. is shown as a function of the shear rate in FIG. 8.

We claim:

1. A composition comprising an oily vehicle and a thickening agent, said thickening agent being incorporated in said oily vehicle in an amount of between about 2 to 10% by weight, calculated on the oily vehicle, and comprising a compound of the general formula wherein
$R^1$ is alkyl with 18 to 36 carbon atoms,
$R^2$ is hydrogen, methyl or a group of the general formula $-(CH_2)_xR^3$,
$R^3$ being a $COOR^4$ group, in which $R^4$ is hydrogen or alkyl with 1 to 4 carbon atoms, or
a $-O[C_rH_{2r}O-]_yR^5$ group, in which $R^5$ is hydrogen, alkyl with 1 to 4 carbon atoms or acyl, r is selected from the group of values consisting of 2,3 and fractions therebetween and $y \geq 0$,
x is a whole number of 2 to 12,
$n \geq 20$ and $m = 0$ to $0.5n$.

2. The composition of claim 1, wherein the oily vehicle is a hydrocarbon oil, an ester oil or a vegetable oil.

3. The composition of claim 1, wherein the oily vehicle is a cosmetic or pharmaceutical preparation.

4. The composition of claim 1, wherein said thickening agent is incorporated in said oily vehicle in an amount of between about 5 to 10% by weight, calculated on the oily vehicle.

5. The composition of claim 1, wherein $R^1$ is alkyl of 22–36 carbon atoms.

6. The composition of claim 1, wherein the acyl of $R^5$ is acetyl.

7. A method of thickening an oily vehicle, such as a hydrocarbon oil, ester oil, vegetable oil, cosmetic preparation or pharmaceutical preparation, said method comprising adding to said vehicle about between 2 to 10% by weight, calculated on the vehicle, of a compound of the general formula wherein
$R^1$ is alkyl with 18 to 36 carbon atoms,
$R^2$ is hydrogen, methyl or a group of the general formula $-(CH_2)_xR^3$,
$R^3$ being a $COOR^4$ group, in which $R^4$ is hydrogen or alkyl with 1 to 4 carbon atoms, or
a $-O[C_rH_{2r}O-]_yR^5$ group, in which $R^5$ is hydrogen, alkyl with 1 to 4 carbon atoms or acyl, r is selected from the group of values consisting of 2,3 and fractions therebetween and $y \geq 0$,
x is a whole number of 2 to 12,
$n \geq 20$ and $m = 0$ to $0.5n$.

8. The method of claim 7, wherein the oily vehicle with said compound incorporated therein, is heated to a temperature above 40° C. to dissolve said compound on the vehicle.

9. The composition of claim 1, wherein the compound is selected from the group consisting of

-continued and

* * * * *